(12) United States Patent
De Matos Gomes et al.

(10) Patent No.: US 12,210,079 B2
(45) Date of Patent: Jan. 28, 2025

(54) PHASE ENCODING WITH FREQUENCY SWEEP PULSES FOR MAGNETIC RESONANCE IMAGING IN INHOMOGENEOUS MAGNETIC FIELDS

(71) Applicant: PROMAXO, INC., Oakland, CA (US)

(72) Inventors: Muller Francis De Matos Gomes, Hayward, CA (US); Aleksandar Nacev, San Francisco, CA (US)

(73) Assignee: Promaxo, Inc., Oakland, CA (US)

( * ) Notice: Subject to any disclaimer, the term of this patent is extended or adjusted under 35 U.S.C. 154(b) by 28 days.

(21) Appl. No.: 17/905,721

(22) PCT Filed: Mar. 9, 2021

(86) PCT No.: PCT/US2021/021464
§ 371 (c)(1),
(2) Date: Sep. 6, 2022

(87) PCT Pub. No.: WO2021/183484
PCT Pub. Date: Sep. 16, 2021

(65) Prior Publication Data
US 2023/0104153 A1    Apr. 6, 2023

Related U.S. Application Data

(60) Provisional application No. 62/987,292, filed on Mar. 9, 2020.

(51) Int. Cl.
*G01V 3/00* (2006.01)
*A61B 5/055* (2006.01)
(Continued)

(52) U.S. Cl.
CPC .......... *G01R 33/4835* (2013.01); *A61B 5/055* (2013.01); *G01R 33/3808* (2013.01); *G01R 33/385* (2013.01)

(58) Field of Classification Search
CPC .............. G01R 33/3415; G01R 33/543; G01R 33/5659; G01R 33/36; A61B 5/055
(Continued)

(56) References Cited

U.S. PATENT DOCUMENTS 5,001,429 A * 3/1991 Constable ............ G01R 33/561
324/307
D895,803 S  9/2020 Nacev et al.
(Continued)

FOREIGN PATENT DOCUMENTS

CN   103654782 A * 3/2014 .......... A61B 5/0555
CN   103885017 A * 6/2014
(Continued)

OTHER PUBLICATIONS

International Search Report and Written Opinion for International PCT Application No. PCT/US2021/021464, dated Jun. 23, 2021.
(Continued)

*Primary Examiner* — Walter L Lindsay, Jr.
*Assistant Examiner* — Frederick Wenderoth
(74) *Attorney, Agent, or Firm* — WILSON SONSINI GOODRICH & ROSATI

(57) ABSTRACT

Single-sided MRI apparatuses, systems, and methods are disclosed. A method can include transmitting a frequency sweep excitation pulse comprising a low-to-high frequency sweep; phase encoding during the frequency sweep excitation pulse; and tuning the amount of phase accumulated during the frequency sweep excitation pulse from adjacent slices in the slab. The frequency sweep excitation pulse can be a chirp pulse. Encoding in this way can prevent spin echoes from drifting and prevent k-space truncation in certain instances. Moreover, the resultant images can be combined more efficiently.

15 Claims, 15 Drawing Sheets

(51) Int. Cl.
*G01R 33/38* (2006.01)
*G01R 33/385* (2006.01)
*G01R 33/483* (2006.01)

(58) Field of Classification Search
USPC .......................................................... 324/309
See application file for complete search history.

(56) References Cited

U.S. PATENT DOCUMENTS

| | | | |
|---|---|---|---|
| D942,012 S | 1/2022 | Nacev et al. | |
| 11,506,737 B2 | 11/2022 | Gomes | |
| D980,981 S | 3/2023 | Nacev et al. | |
| 11,609,291 B2 | 3/2023 | Nacev et al. | |
| 11,656,303 B2 | 5/2023 | Nacev et al. | |
| 2007/0222433 A1* | 9/2007 | Tiernan | G01R 33/5617 324/318 |
| 2011/0084206 A1* | 4/2011 | Neuberth | G01R 33/3815 324/307 |
| 2014/0218028 A1 | 8/2014 | Snyder et al. | |
| 2018/0356480 A1 | 12/2018 | Weinberg et al. | |
| 2022/0113361 A1 | 4/2022 | Nacev et al. | |
| 2022/0146613 A1 | 5/2022 | Gomes | |
| 2022/0342020 A1 | 10/2022 | Narayanan et al. | |
| 2023/0106912 A1 | 4/2023 | Kumar et al. | |
| 2023/0109705 A1 | 4/2023 | De Matos Gomes | |
| 2023/0110217 A1 | 4/2023 | Nacev et al. | |
| 2023/0184856 A1 | 6/2023 | Nacev et al. | |
| 2023/0296707 A1 | 9/2023 | Gomes et al. | |

FOREIGN PATENT DOCUMENTS

| | | | | |
|---|---|---|---|---|
| DE | 102011007148 A1 * | 10/2012 | ............. | A61N 5/103 |
| EP | 0399789 A2 | 11/1990 | | |
| WO | WO-2010114959 A1 * | 10/2010 | ........... | A61B 5/0051 |
| WO | WO-2020168233 A1 | 8/2020 | | |
| WO | WO-2020172672 A1 | 8/2020 | | |
| WO | WO-2020172673 A1 | 8/2020 | | |
| WO | WO-2020198395 A1 | 10/2020 | | |
| WO | WO-2020198396 A1 | 10/2020 | | |
| WO | WO-2020264194 A1 | 12/2020 | | |
| WO | WO-2021150902 A1 | 7/2021 | | |
| WO | WO-2021168291 A2 | 8/2021 | | |
| WO | 2021183484 A1 | 9/2021 | | |
| WO | WO-2021183482 A1 | 9/2021 | | |

OTHER PUBLICATIONS

Ben-Eliezer et al., Spatiotemporal encoding as a robust bases for fast three-dimensional in vivo MRI, NMR in Biomedicine (Feb. 24, 2011), 24:1191-1201.

Tal et al., Spatial encoding and the single-scan acquisition of high definition MR images in inhomogeneous fields, Journal of Magnetic Resonance (Jul. 14, 2006), 182:179-194.

International Preliminary Report on Patentability for International PCT Application No. PCT/US2021/021464, dated Sep. 22, 2022.

* cited by examiner

PHASE ENCODING WITH FREQUENCY SWEEP PULSES FOR MAGNETIC RESONANCE IMAGING IN INHOMOGENEOUS MAGNETIC FIELDS

CROSS-REFERENCE TO RELATED APPLICATIONS

This application is a U.S. National Stage Entry under 35 U.S.C. § 371 of International Patent Application No. PCT/US2021/021464, entitled PHASE ENCODING WITH FREQUENCY SWEEP PULSES FOR MAGNETIC RESONANCE IMAGING IN INHOMOGENEOUS MAGNETIC FIELDS, filed Mar. 9, 2021, which claims the benefit under 35 U.S.C. § 119(e) to U.S. Provisional Patent Application No. 62/987,292, titled SYSTEMS AND METHODS FOR LIMITING k-SPACE TRUNCATION IN A SINGLE-SIDED MRI SCANNER, filed Mar. 9, 2020, the entire disclosures of which are hereby incorporated by reference herein.

BACKGROUND

Single-sided or open magnetic resonance imaging (MRI) scanners generally have a permanent or inherent gradient magnetic field along a longitudinal axis extending from the single-sided MRI apparatus into a field of view. The permanent gradient magnetic field can be produced by rare earth magnets and two sets of gradient coils on the face of the permanent magnets. This orientation allows imaging within a field of view above the face of the magnet. By designing a system with this form factor, it is possible to image without having to enclose the region being imaged. So, one may then image without having a patient enter a bore, allowing for the scanner to be used with other medical devices, such as a biopsy robot, for example. It is also more comfortable for claustrophobic patients to be imaged outside an imaging bore of a conventional, enclosed MRI scanner. Single-sided MRIs can also be portable and can image anything positioned within the field of view.

The use of a surface gradient coil with a single-sided scanner, though generally needed for one-sided scanning, can result in a changing field of view along the Z axis, a drifting echo, and/or ultimately in the truncation of k-space, which may cause blurring and effectively limit the image quality obtained by the single-sided MRI scanner.

SUMMARY

In one aspect of the present disclosure, a method of imaging a slab having at least two slices with a single-sided magnetic imaging apparatus defining an inherent gradient magnetic field extending from the magnetic imaging apparatus into a field of view, comprises transmitting a frequency sweep excitation pulse comprising a low-to-high frequency sweep; phase encoding during the frequency sweep excitation pulse; and tuning the amount of phase accumulated during the frequency sweep excitation pulse from adjacent slices in the slab.

In another aspect of the present disclosure, a magnetic imaging apparatus, comprising a permanent magnet, a gradient coil set, an electromagnet, a radio frequency coil, wherein an inherent gradient magnetic field extends from the magnetic imaging apparatus relative to a first axis into the field of view, wherein the first axis is perpendicular to the permanent magnet, and a control circuit configured for imaging a slab having at least two slices, wherein the imaging comprises: transmitting a frequency sweep excitation pulse comprising a low-to-high frequency sweep; phase encoding during the frequency sweep excitation pulse; and tuning the amount of phase accumulated during the frequency sweep excitation pulse from adjacent slices in the slab.

BRIEF DESCRIPTION OF THE DRAWINGS

The novel features of the various aspects are set forth with particularity in the appended claims. The described aspects, however, both as to organization and methods of operation, may be best understood by reference to the following description, taken in conjunction with the accompanying drawings.

Figure 2:
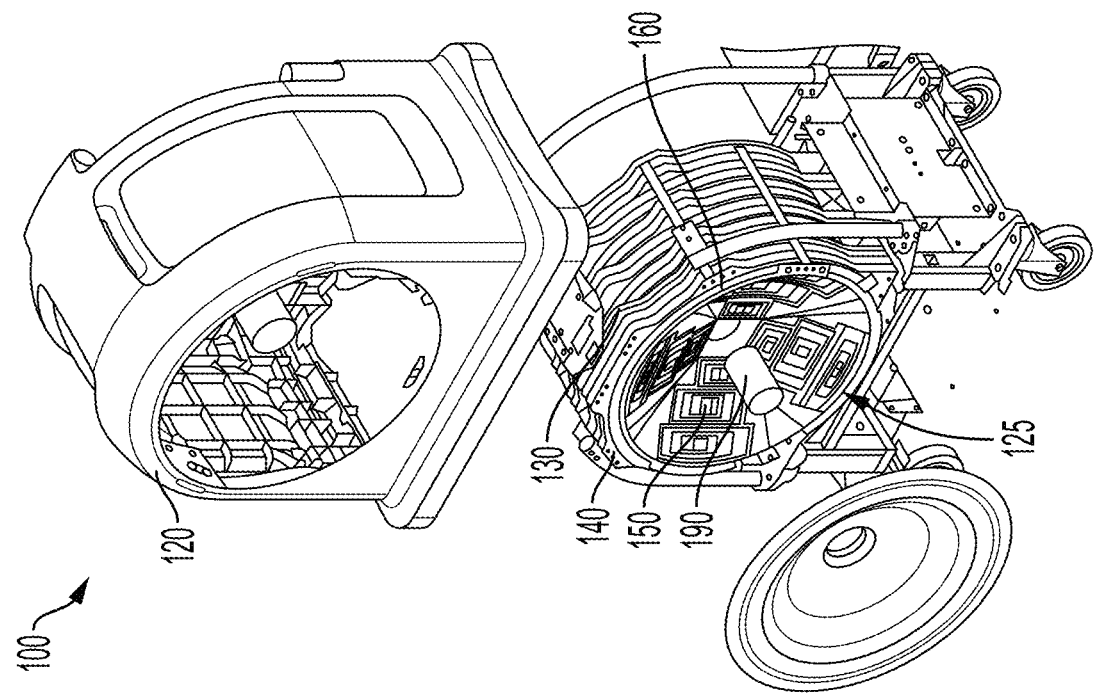
FIG. 2 is an exploded, perspective view of the MRI scanner of FIG. 1, in which the permanent magnet assembly and the gradient coil sets within the housing are exposed, according to various aspects of the present disclosure.

The accompanying drawings are not intended to be drawn to scale. Corresponding reference characters indicate corresponding parts throughout the several views. For purposes of clarity, not every component may be labeled in every drawing. The exemplifications set out herein illustrate certain embodiments of the invention, in one form, and such exemplifications are not to be construed as limiting the scope of the invention in any manner.

DETAILED DESCRIPTION

Applicant also owns International Patent Application titled PULSE SEQUENCES AND FREQUENCY SWEEP PULSES FOR SINGLE-SIDED MAGNETIC RESONANCE IMAGING, filed Mar. 9, 2021, which claims priority to U.S. Provisional Patent Application No. 62/987,286, titled SYSTEMS AND METHODS FOR ADAPTING DRIVEN EQUILIBRIUM FOURIER TRANSFORM FOR SINGLE-SIDED MRI, filed Mar. 9, 2020, both of which are incorporated by reference herein in their respective entireties.

The following international patent applications are incorporated by reference herein in their respective entireties:

International Application No. PCT/US2020/018352, titled SYSTEMS AND METHODS FOR ULTRALOW FIELD RELAXATION DISPERSION, filed Feb. 14, 2020, now International Publication No. WO2020/168233;

International Application No. PCT/US2020/019530, titled SYSTEMS AND METHODS FOR PERFORMING MAGNETIC RESONANCE IMAGING, filed Feb. 24, 2020, now International Publication No. WO2020/172673;

International Application No. PCT/US2020/019524, titled PSEUDO-BIRDCAGE COIL WITH VARIABLE TUNING AND APPLICATIONS THEREOF, filed Feb. 24, 2020, now International Publication No. WO2020/172672;

International Application No. PCT/US2020/024776, titled SINGLE-SIDED FAST MRI GRADIENT FIELD COILS AND APPLICATIONS THEREOF, filed Mar. 25, 2020, now International Publication No. WO2020/198395;

International Application No. PCT/US2020/024778, titled SYSTEMS AND METHODS FOR VOLUMETRIC ACQUISITION IN A SINGLE-SIDED MRI SYSTEM, filed Mar. 25, 2020, now International Publication No. WO2020/198396;

International Application No. PCT/US2020/039667, title SYSTEMS AND METHODS FOR IMAGE RECONSTRUCTIONS IN MAGNETIC RESONANCE IMAGING, filed Jun. 25, 2020, now International Publication No. WO2020/264194;

International Application No. PCT/US2021/014628, titled MRI-GUIDED ROBOTIC SYSTEMS AND METHODS FOR BIOPSY, filed Jan. 22, 2021; and International Application No. PCT/US2021/018834, titled RADIO FREQUENCY RECEPTION COIL NETWORKS FOR SINGLE-SIDED MAGNETIC RESONANCE IMAGING, filed Feb. 19, 2021.

U.S. Patent Application Publication No. 2018/0356480, titled UNILATERAL MAGNETIC RESONANCE IMAGING SYSTEM WITH APERTURE FOR INTERVENTIONS AND METHODOLOGIES FOR OPERATING SAME, published Dec. 13, 2018, is incorporated by reference herein in its entirety.

Before explaining various aspects of an MRI system and methods in detail, it should be noted that the illustrative examples are not limited in application or use to the details of construction and arrangement of parts illustrated in the accompanying drawings and description. The illustrative examples may be implemented or incorporated in other aspects, variations, and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects, and/or examples.

In accordance with various aspects, an MRI system is provided that can include a unique imaging region that can be offset from the face of a magnet. Such offset and single-sided MRI systems are less restrictive as compared to traditional MRI scanners. In addition, this form factor can have a built-in or inherent magnetic field gradient that creates a range of magnetic field values over the region of interest. In other words, the inherent magnetic field can be inhomogeneous. The inhomogeneity of the magnetic field strength in the region of interest for the single-sided MRI system can be more than 200 parts per million (ppm). For example, the inhomogeneity of the magnetic field strength in the region of interest for the single-sided MRI system can between 200 ppm and 200,000 ppm. In various aspects of the present disclosure, the inhomogeneity in the region of interest can be greater than 1,000 ppm and can be greater than 10,000 ppm. In one instance, the inhomogeneity in the region of interest can be 81,000 ppm.

The inherent magnetic field gradient can be generated by a permanent magnet within the MRI scanner. The magnetic field strength in the region of interest for the single-sided MRI system can be less than 1 Tesla (T), for example. For example, the magnetic field strength in the region of interest for the single-sided MRI system can be less than 0.5 T. In other instances, the magnetic field strength can be greater than 1 T and may be 1.5 T, for example. This system can operate at a lower magnetic field strength as compared to typical MRI systems allowing for a relaxation on the RX coil design constraints and/or allowing for additional mechanisms, like robotics, for example, to be used with the MRI scanner. Exemplary MRI-guided robotic systems are further described in International Application No. PCT/US2021/014628, titled MRI-GUIDED ROBOTIC SYSTEMS AND METHODS FOR BIOPSY, filed Jan. 22, 2021, for example.

Figure 1:
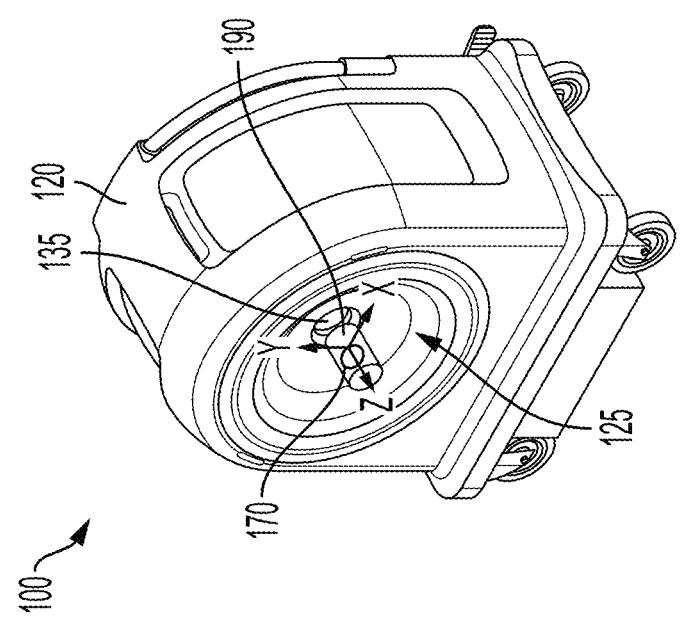
FIG. 1 is a perspective view of an MRI scanner, according to various aspects of the present disclosure.

FIGS. 1-6 depict an MRI scanner 100 and components thereof. As shown in FIGS. 1 and 2, the MRI scanner 100 includes a housing 120 having a face or front surface 125, which is concave and recessed. In other aspects, the face of the housing 120 can be flat and planar. The front surface 125 can face the object being imaged by the MRI scanner. As shown in FIGS. 1 and 2, the housing 120 includes a permanent magnet assembly 130, an RF transmission coil (TX) 140, a gradient coil set 150, an electromagnet 160, and a RF reception coil (RX) 170. In other instances, the housing 120 may not include the electromagnet 160. Moreover, in certain instances, the RF reception coil 170 and the RF transmission coil 140 can be incorporated into a combined Tx/Rx coil array.

Figure 4:
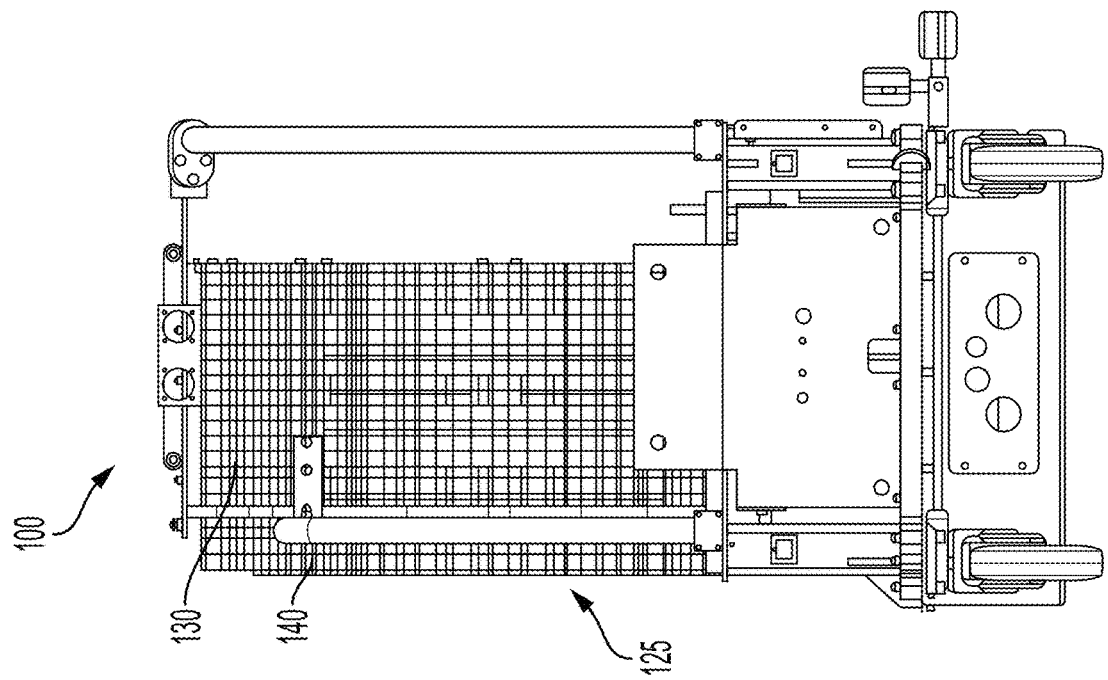
FIG. 4 is an elevation view of the MRI scanner of FIG. 1, according to various aspects of the present disclosure.
Figure 3:
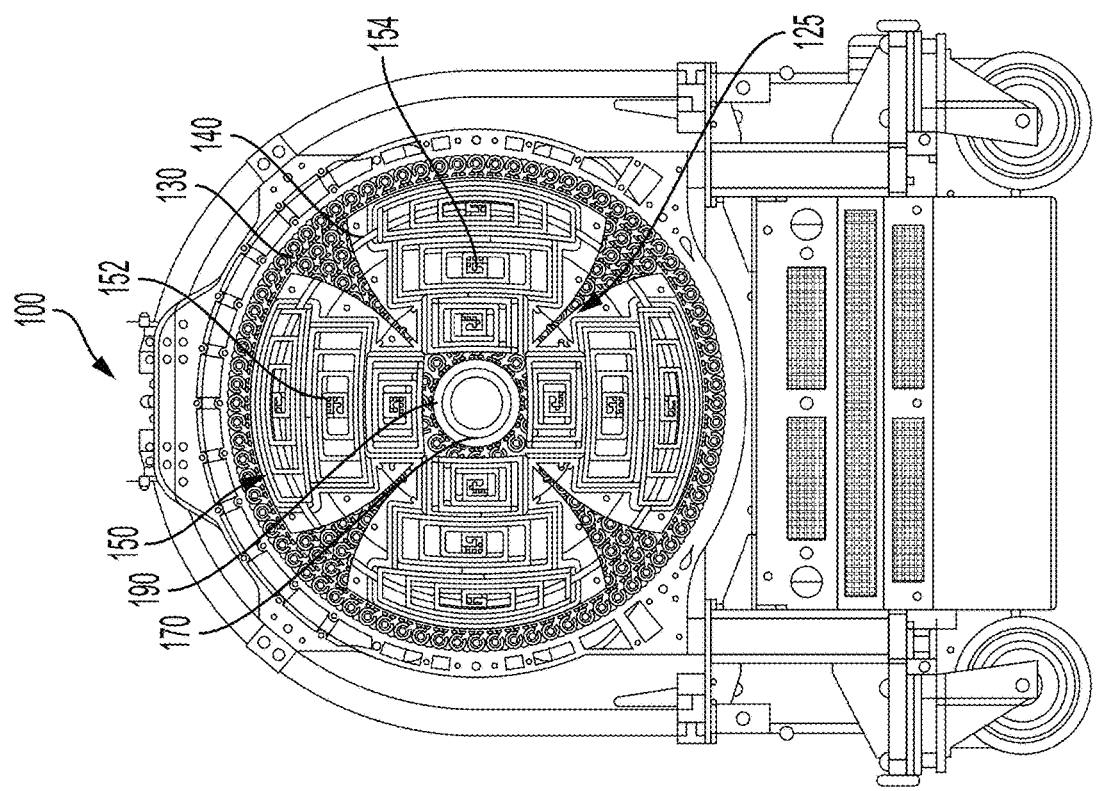
FIG. 3 is an elevation view of the MRI scanner of FIG. 1, according to various aspects of the present disclosure.
Figure 5:
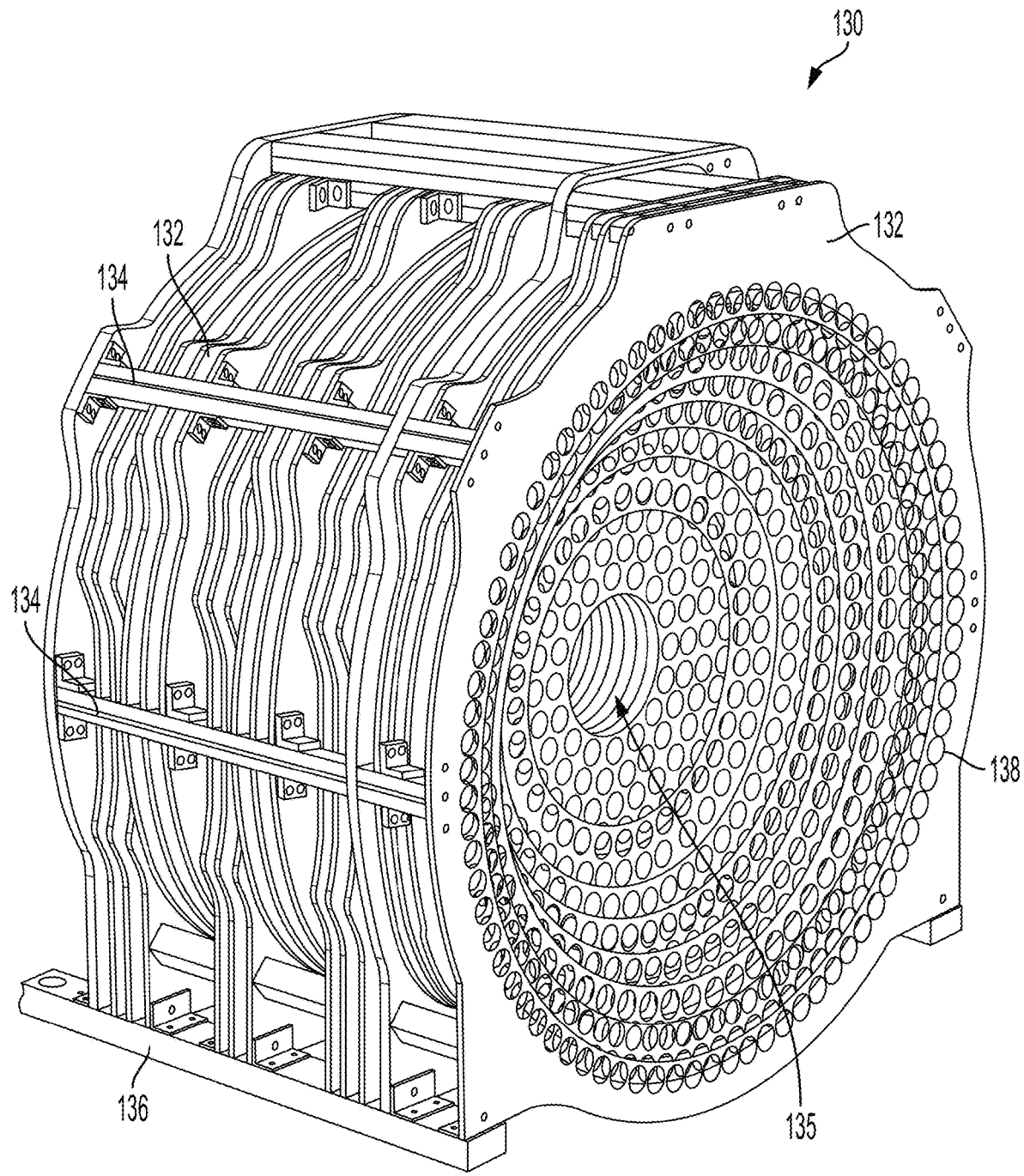
FIG. 5 is a perspective view of the permanent magnet assembly of the MRI scanner of FIG. 1, according to various aspects of the present disclosure.
Figure 6:
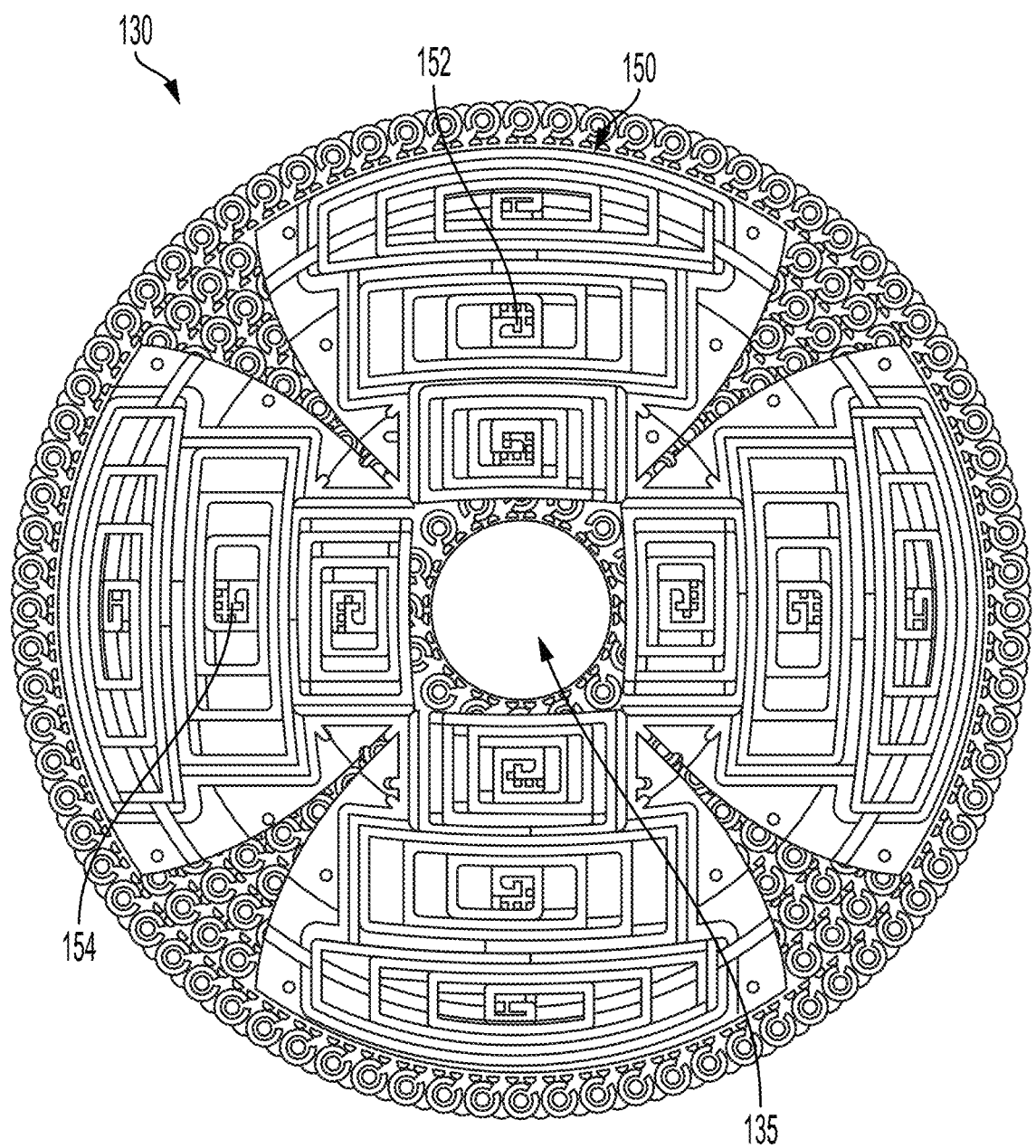
FIG. 6 is an elevation view of the gradient coil set and the permanent magnet assembly of the MRI system shown in FIG. 1, according to various aspects of the present disclosure.

Referring primarily to FIGS. 3-5, the permanent magnet assembly 130 includes an array of magnets. The array of magnets forming the permanent magnet assembly 130 are configured to cover the front surface 125, or patient-facing surface, of the MRI scanner 100 (see FIG. 3) and are shown as horizontal bars in FIG. 4. The permanent magnet assembly 130 includes a plurality of cylindrical permanent magnets in a parallel configuration. Referring primarily to FIG. 5, the permanent magnet assembly 130 comprises parallel plates 132 that are held together by brackets 134. The system can be attached to the housing 120 of the MRI scanner 100 at a bracket 136. There can be a plurality of holes 138 in the parallel plates 132. The permanent magnet assembly 130 can include any suitable magnetic materials, including but not limited to rare-earth based magnetic materials, such as for example, Neodymium-based magnetic materials, for example.

The permanent magnet assembly 130 defines an access aperture or bore 135, which can provide access to the patient through the housing 120 from the opposite side of the housing 120. In other aspects of the present disclosure, the array of permanent magnets forming a permanent magnet assembly in the housing 120 may be bore-less and define an uninterrupted or contiguous arrangement of permanent magnets without a bore defined therethrough. In still other instances, the array of permanent magnets in the housing 120 may form more than one bore/access aperture therethrough.

In accordance with various aspects of the present disclosure, the permanent magnet assembly 130 provides a magnetic field B0 in a region of interest 190 that is along the Z axis, shown in FIG. 1. The Z axis is perpendicular to the permanent magnet assembly 130. Stated differently, the Z axis extends from a center of the permanent magnet assembly 130 and defines a direction of the magnetic field B0 away from the face of the permanent magnet assembly 130. The Z axis can define the primary magnetic field B0 direction. The primary magnetic field B0 can decrease along the Z axis, i.e. an inherent gradient, farther from the face of the permanent magnet assembly 130 and in the direction indicated with the arrow in FIG. 1.

In one aspect, the inhomogeneity of the magnetic field in the region of interest 190 for the permanent magnet assembly 130 can be approximately 81,000 ppm. In another aspect, the inhomogeneity of the magnetic field strength in the region of interest 190 for the permanent magnet assembly 130 can be between 200 ppm to 200,000 ppm and can be greater than 1,000 ppm in certain instances, and greater than 10,000 ppm in various instances.

In one aspect, the magnetic field strength of the permanent magnet assembly 130 can be less than 1 T. In another aspect, the magnetic field strength of the permanent magnet assembly 130 can be less than 0.5 T. In other instances, the magnetic field strength of the permanent magnet assembly 130 can be greater than 1 T and may be 1.5 T, for example. Referring primarily to FIG. 1, the Y axis extends up and down from the Z axis and the X axis extends to the left and right from the Z axis. The X axis, the Y axis, and the Z axis are all orthogonal to one another and the positive direction of each axis is indicated by the corresponding arrow in FIG. 1.

The RF transmission coils 140 are configured to transmit RF waveforms and associated electromagnetic fields. The RF pulses from the RF transmission coils 140 are configured to rotate the magnetization produced by the permanent magnet 130 by generating an effective magnetic field, referred to as B1, that is orthogonal to the direction of the permanent magnetic field (e.g. an orthogonal plane).

Referring primarily to FIG. 3, the gradient coil set 150 includes two sets of gradient coils 152, 154. The sets of gradient coils 152, 154 are positioned on the face or front surface 125 of the permanent magnet assembly 130 intermediate the permanent magnet assembly 130 and the region of interest 190. Each set of gradient coils 152, 154 includes a coil portion on opposing sides of the bore 135. Referring to the axes in FIG. 1, the gradient coil set 154 may be the gradient coil set corresponding to the X axis, for example, and the gradient coil set 152 may be the gradient coil set corresponding to the Y axis, for example. The gradient coils 152, 154 enable encoding along the X axis and Y axis, as further described herein.

Figure 7:
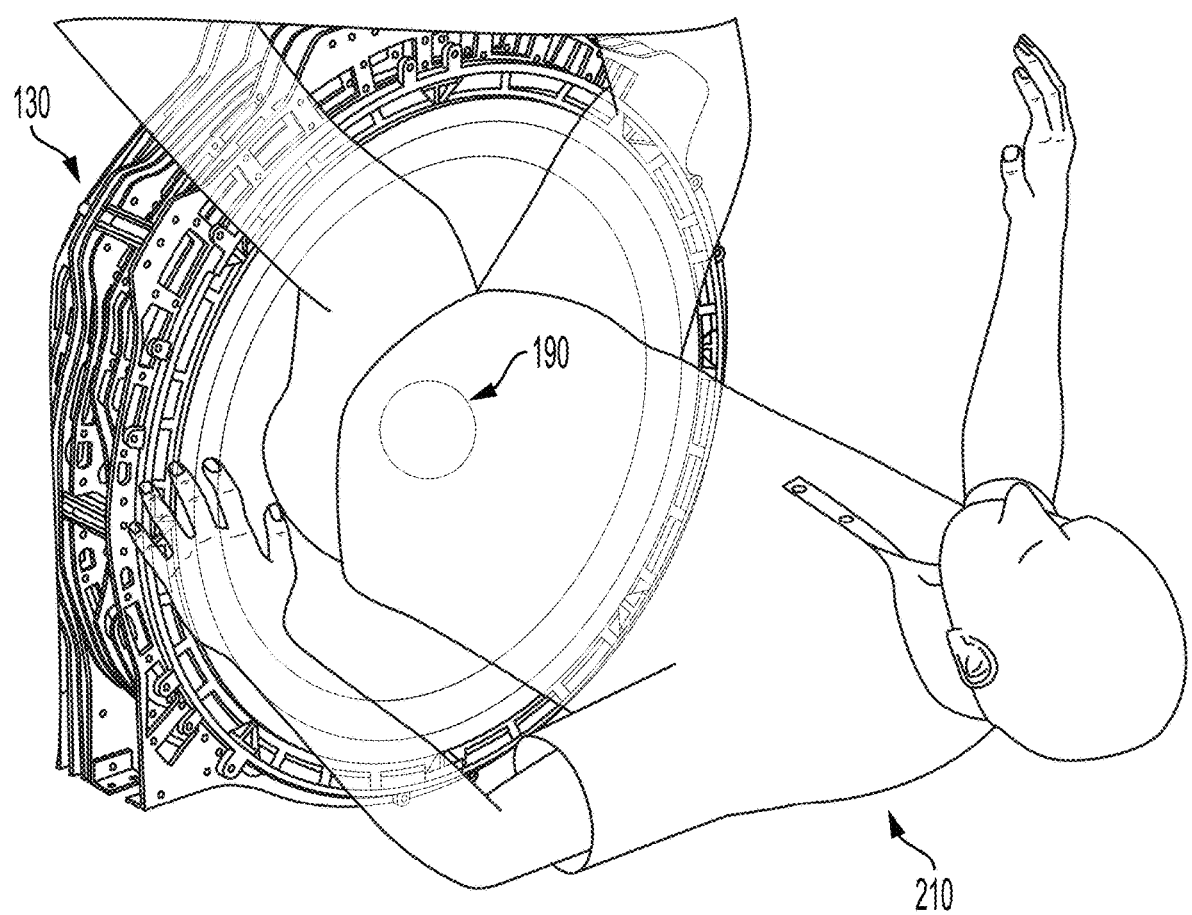
FIG. 7 illustrates exemplary positioning of a patient for imaging by a single-sided MRI scanner for certain surgical procedures and interventions, according to various aspects of the present disclosure.

In accordance with various aspects, using the MRI scanner 100 illustrated in FIGS. 1-6, a patient can be positioned in any number of different positions depending on the type of anatomical scan. FIG. 7 shows an example where the pelvis is scanned with the MRI scanner 100. To perform the scan, a patient 210 can be laid on a surface in a lithotomy position. As illustrated in FIG. 7, for the pelvic scan, the patient 210 can be positioned to have their back resting on a table and legs raised up to be resting against the top of the scanner 100. The pelvic region can be positioned directly in front of the permanent magnet assembly 130 and the bore 135 and the region of interest 190 is in the pelvic region of the patient 210.

Figure 8:
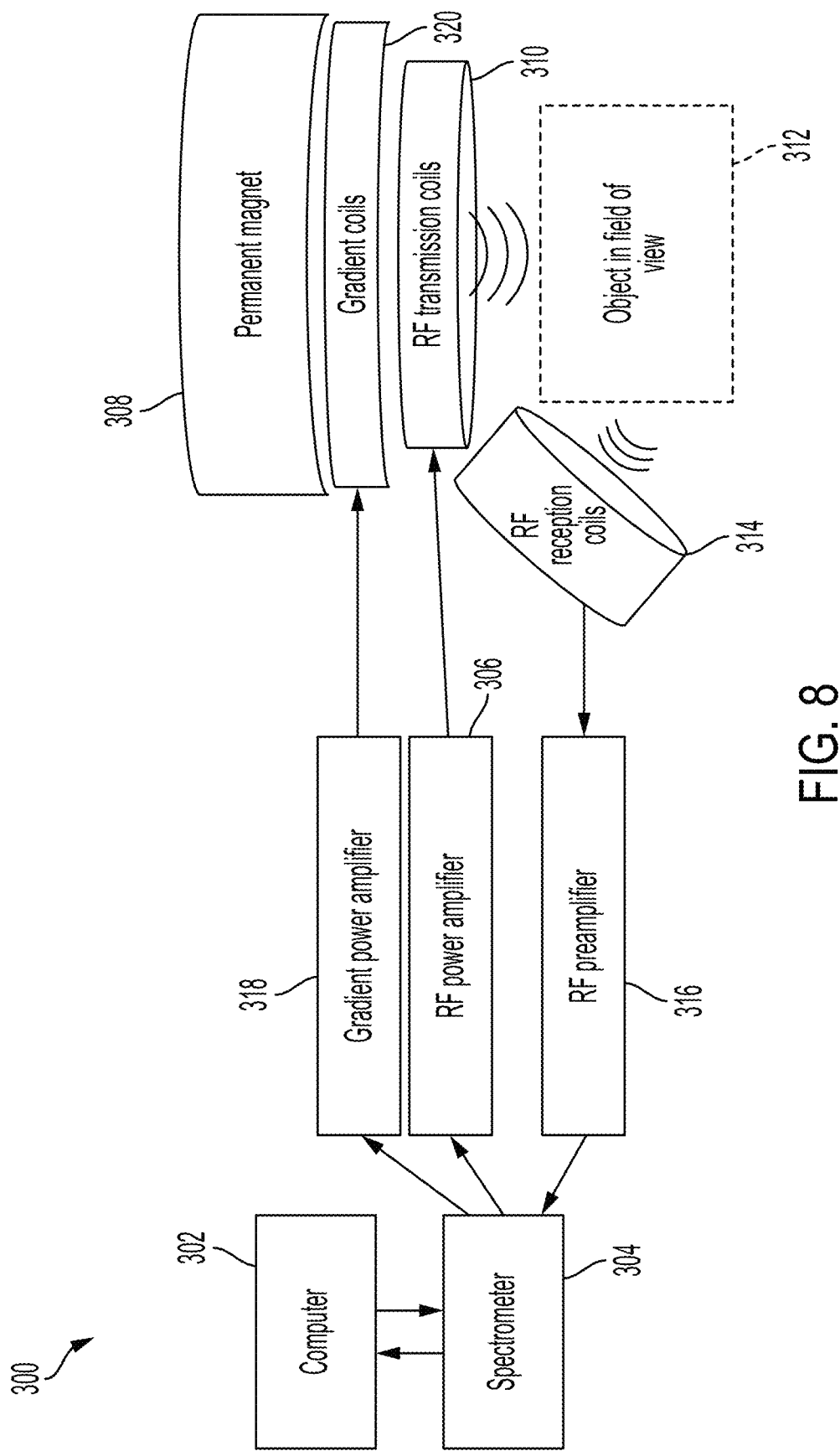
FIG. 8 is a control schematic for a single-sided MRI system, according to various aspects of the present disclosure.

Referring now to FIG. 8, a control schematic for a single-sided MRI system 300 is shown. The single-sided MRI scanner 100 and/or components thereof (FIGS. 1-6) can be incorporated into the MRI system 300 in various aspects of the present disclosure. For example, the imaging system 300 includes a permanent magnet assembly 308, which can be similar to the permanent magnet assembly 130 (see FIGS. 2-5) in various instances. The imaging system 300 also includes RF transmission coils 310, which can be similar to the RF transmission coil 140 (see FIG. 3), for example. Moreover, the imaging system 300 includes RF reception coils 314, which can be similar to the RF reception coils 170 (see FIG. 3), for example. In various aspects, the RF transmission coils 310 and/or the RF reception coils can also be positioned in the housing of an MRI scanner and, in certain instances, the RF transmission coils 310 and the RF reception coils 314 can be combined into integrated Tx/Rx coils. The system 300 also includes gradient coils 320, which are configured to generate gradient fields to facilitate imaging of the object in the field of view 312.

The single-sided MRI system 300 also includes a computer 302, which is in signal communication with a spectrometer 304, and is configured to send and receive signals between the computer 302 and the spectrometer 304.

The main magnetic field B0 generated by the permanent magnet 308 extends away from the permanent magnet 308 and away from the RF transmission coils 310 into the field of view 312. The field of view 312 contains an object that is being imaged by the MRI system 300.

During the imaging process, the main magnetic field B0 extends into the field of view 312. The direction of the effective magnetic field (B1) changes in response to the RF pulses and associated electromagnetic fields from the RF transmission coils 310. For example, the RF transmission coils 310 are configured to selectively transmit RF signals or pulses to an object in the field of view, e.g. tissue. These RF pulses alter the effective magnetic field experienced by the spins in the sample (e.g. patient tissue). When the RF pulses are on, the effective field experienced by spins on resonance is solely the RF pulse, effectively canceling the static B0 field. The RF pulses can be chirp or frequency sweep pulses, for example, as further described herein.

Moreover, when the object in the field of view 312 is excited with RF pulses from the RF transmission coils 310, the precession of the object results in an induced electric current, or MR current, which is detected by the RF reception coils 314. The RF reception coils 314 can send the excitation data to an RF preamplifier 316. The RF preamplifier 316 can boost or amplify the excitation data signals and send them to the spectrometer 304. The spectrometer 304 can send the excitation data to the computer 302 for storage, analysis, and image construction. The computer 302 can combine multiple stored excitation data signals to create an image, for example.

From the spectrometer 304, signals can also be relayed to the RF transmission coils 310 via an RF power amplifier 306, and to the gradient coils 320 via a gradient power amplifier 318. The RF power amplifier 306 amplifies the signal and sends it to RF transmission coils 310. The gradient power amplifier 318 amplifies the gradient coil signal and sends it to the gradient coils 320.

Systems and methods for effectively collecting nuclear magnetic resonance spectra and magnetic resonance images in inhomogeneous fields, such as with the single-sided MRI scanner 100 and system 300, for example, are described herein.

Imaging with a single-sided or open MRI presents many challenges. Typically, two sets of gradient coils (see FIG. 6) in single-sided systems are placed on the face of the permanent magnet assembly. As a result, the amplitude of the gradient will drop as one moves away from the face of the permanent magnet assembly. So, for a given array of phase encodes, the field of view will change as one moves along the axis of the permanent magnetic field B0. In other words, the pulsed gradient coils in a single-sided scanner have a small component along the direction of the permanent gradient.

Figure 9:
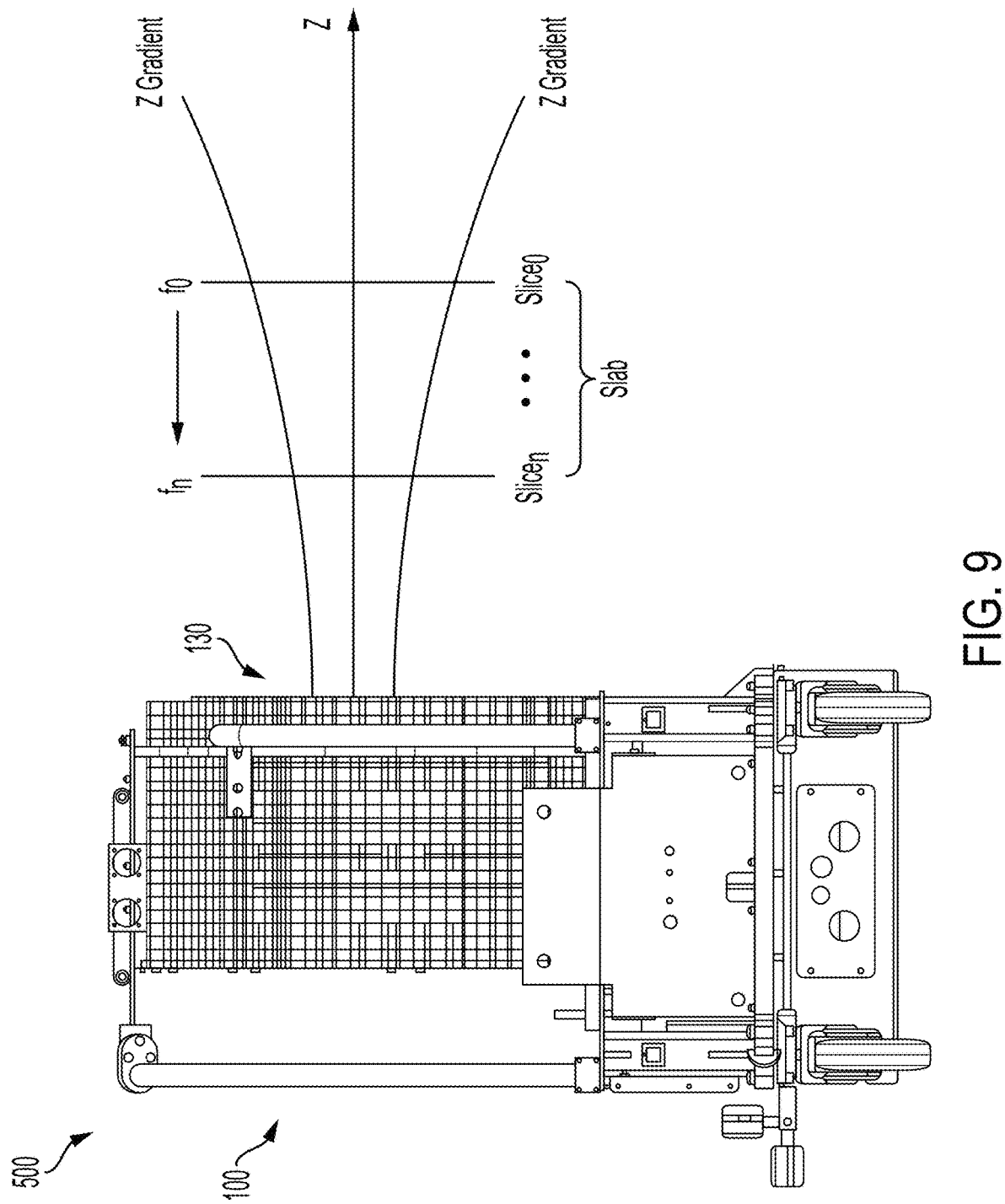
FIG. 9 is a schematic of the magnetic gradient along the Z axis, according to various aspects of the present disclosure.

FIG. 9 is a schematic 500 of the magnetic field gradient along the Z axis for the MRI scanner 100. The permanent magnet 130 has an inherent gradient along the Z axis. The strength of the Z gradient decreases as one moves away from the permanent magnet 130. The Z gradient can be seen in the schematic bending away as one moves away from the permanent magnet causing the strength of the gradient to decrease. The MRI scanner 100 images multiple slices to create a slab. Each slice is excited for imaging at a different frequency. The lower frequencies excite tissue for slices farther away from the permanent magnet and higher frequencies excite the tissue in slices closer to the magnet. In the schematic, the slab or axial image is made of multiple slices going from $Slice_0$ to $Slice_n$. Each slice has a corresponding frequency $f_0$ to $f_n$, where $f_0$ is a frequency that is smaller than $f_n$.

Due to how the gradient changes along the Z axis each slice has a different field of view. The changing field of view causes the same object in different slices to appear to shrink and grow along slices in the Z dimension because the magnitude of the gradient also varies along the Z axis. This results in images appearing blurrier when they are converted into axial images due to them being comprised of several different size images collapsed together. Thus, the slices in the slab need to have the same field of view and the same scale to produce a high-quality axial image. Additionally, there are magnetic gradients in the Y axis and the X axis created by the gradient coils and the gradients are shaped similarly and have a similar effect along the X and Y axes.

Figure 10:
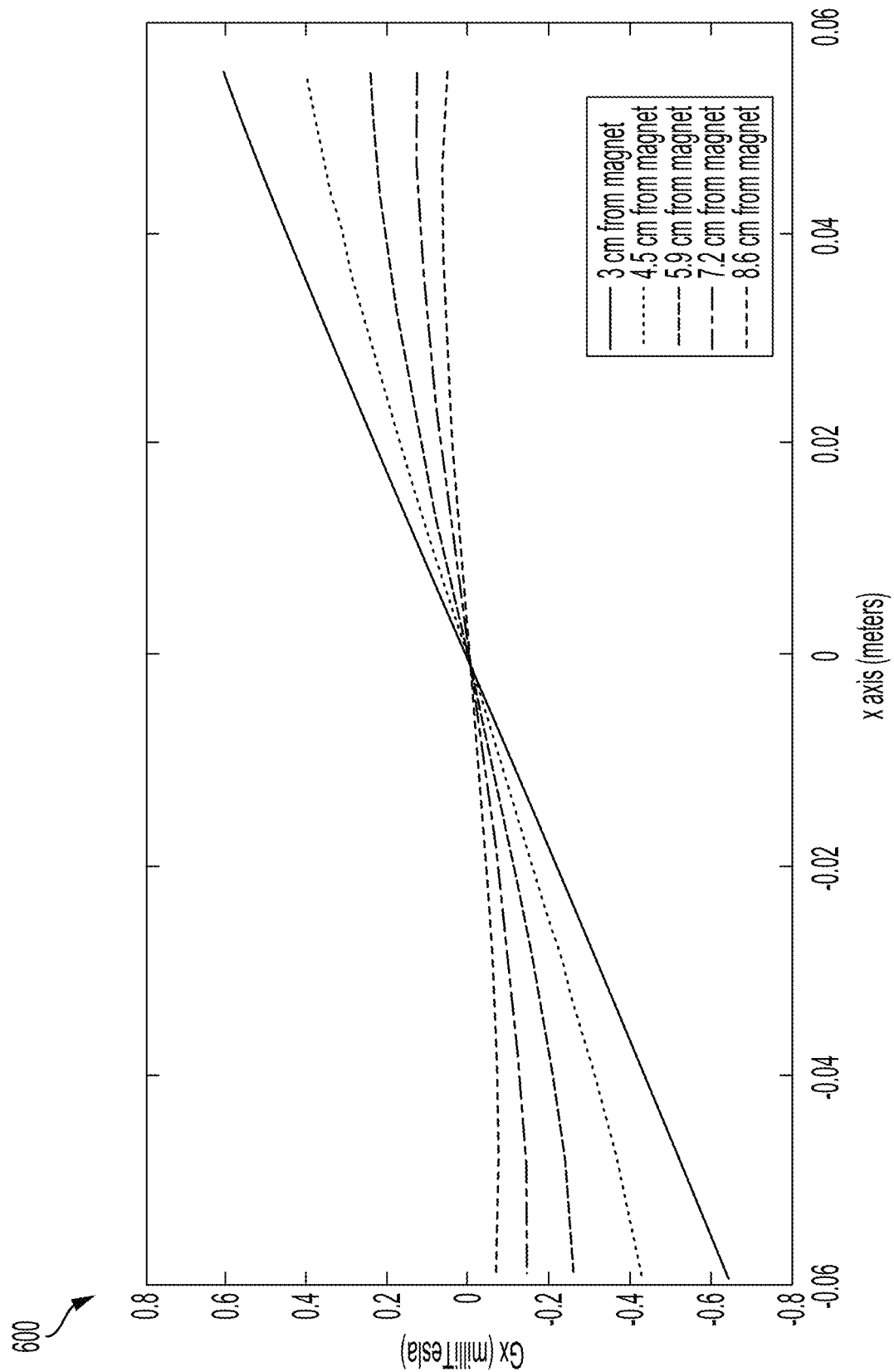
FIG. 10 is a graphical representation of the X gradient along the X axis, according to various aspects of the present disclosure.

Referring to FIG. 10, a graphical representation 600 provides an example of how the X gradient changes as you move along the X axis. Changes in the X gradient due to movement along the axis are shown as the different lines types, which range from a distance of 3 cm to 8.6 cm along the Z axis. In other words, the slope of the gradient will change depending on the distance from the face of the magnet. The magnitude of the change can be significant. In other words, the object size in the image can change by as much as a factor of 2 over just 1 inch of movement along the Z axis. The zero on the X axis is in the center of the magnet along the Z axis. As one moves away from the Z axis moving along the X axis the value of the gradient can change significantly. The farther one moves along the X axis the greater the gradient magnitude becomes.

To reiterate, the implications of the gradient magnetic fields in single-sided MRI scanners are noteworthy. For example, exciting a thick slice of an object (e.g. tissue) along the longitudinal axis of the permanent gradient (i.e., the Z axis), will result in the scale or imaged size of the object to change as one moves along Z axis. A 3D image with any thickness along the Z axis will be scaled to a smaller size, i.e. will appear to shrink, at lower frequency slices, which are slices positioned further from the permanent magnet. This results in significant blurring of the image when adjacent slices are then combined together, because features of different sizes are superimposed on one another.

Figure 11:
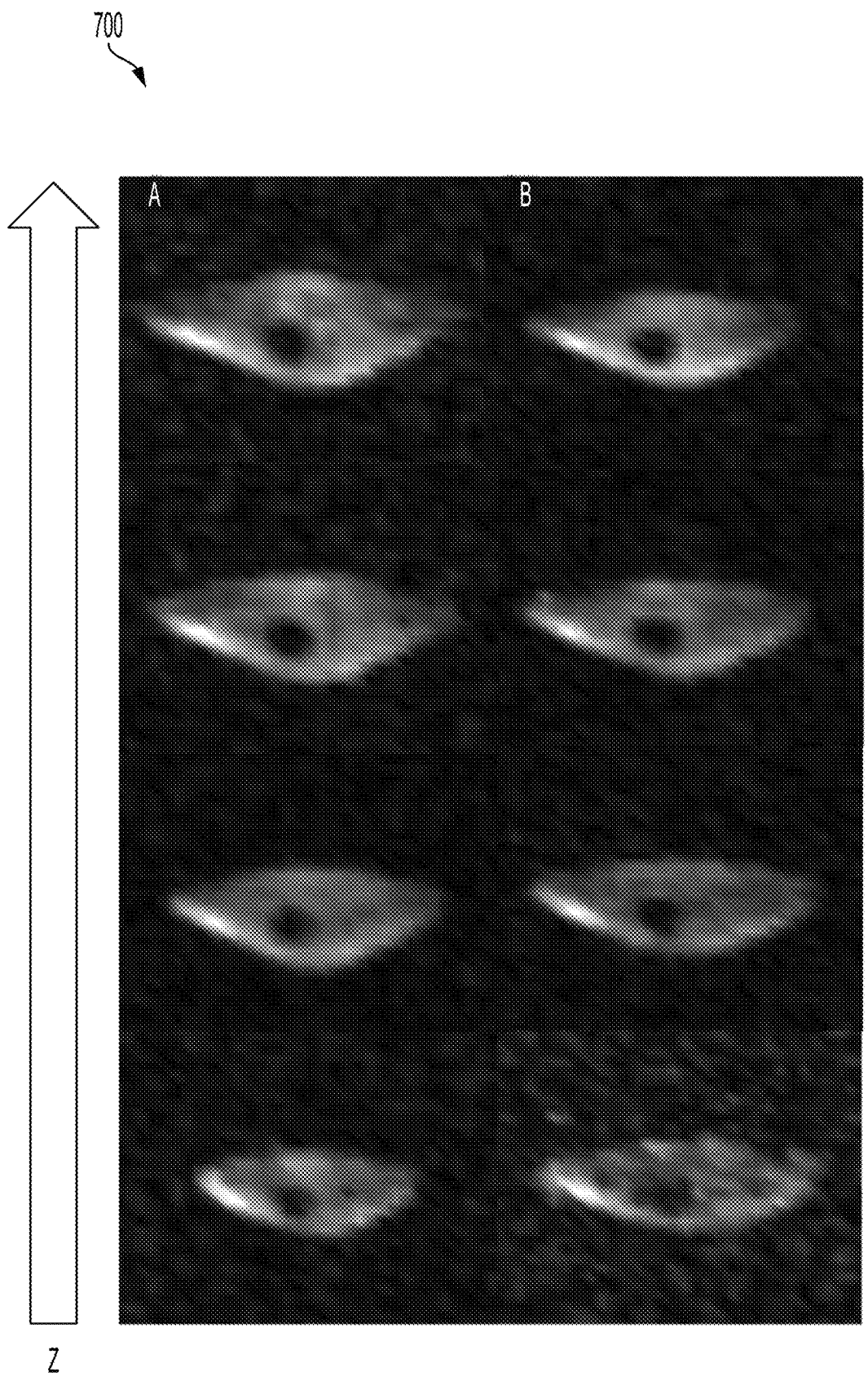
FIG. 11 is a collection of MRI images comparing image slices that account for the changing field of view along the Z axis and image slices that do not account for the changing field of view along the Z axis, according to various aspects of the present disclosure.

As a result of the gradients changing as you move farther from the magnet, the field of view will change as one moves from the face of the magnet. Combining slices with different field of views into a slab results in features becoming blurred. FIG. 11 shows MRI image slices, where one set accounts for the changing field of view along the Z axis and one set does not. In other words, the diagram 700 shows how the scale of an object being scanned can change if you do not account for the changing field of view along the Z axis. Slices in column A (left) show the structure changing in size as one moves along the Z axis. Column B (right) shows the structure staying close to the same size because the changing field of view has been appropriated accounted for.

The size of the object in column A becomes greater as one moves farther away from the permanent magnet along the Z axis due to the Z gradient. Combining these slices into an axial image or slab results in a blurry image because the size of the object in adjacent slices has changed due to the field of view changing. Stated another way, objects will appear to shrink and grow along the Z dimension because the magnitude of the gradient also varies along z. This results in images appearing blurrier when they are converted into axial images or slabs due to them being comprised of several different size images collapsed together. By accounting for the field of view changing the scale of the object remains close to the same and results in a much clearer image when combined into a slab.

An additional implication of the permanent gradient magnetic field of a single-sided MRI systems, beyond the varying field of view, is the changing location of the spin echo during image encoding with a surface gradient coil. In single-sided MRI system, image encoding is done by phase encoding; frequency encoding is done with just the permanent gradient. Signals collected with a single-sided MRI system are some variation of a spin echo, with the acquisition window of the MRI scanner set to place the echo in the middle. In order to form an echo, the phase that is accumulated after excitation must be refocused by the time the acquisition begins.

Figure 12:
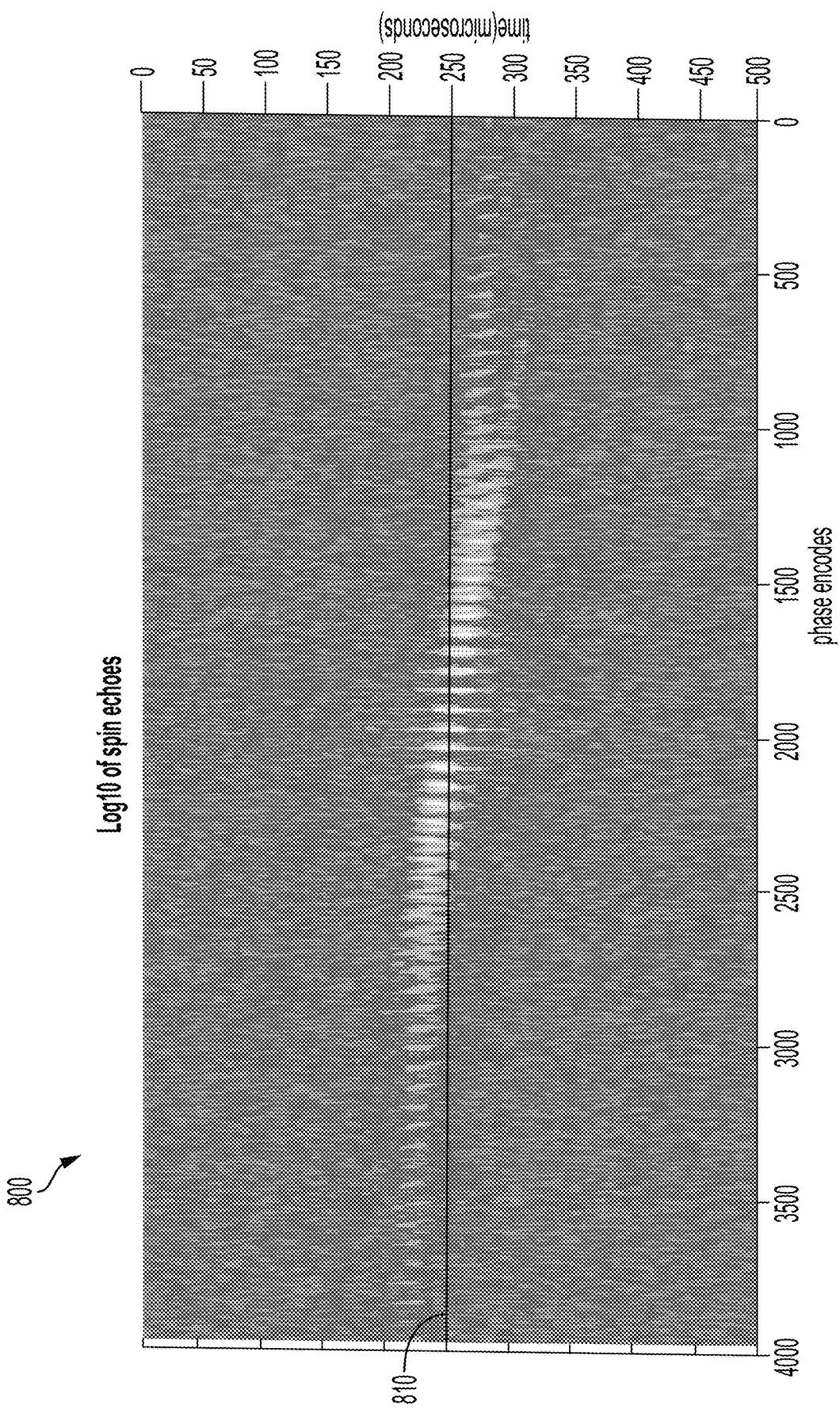
FIG. 12 is a graphical representation of the location of the echoes in time as one moves through the phase table, according to various aspects of the present disclosure.

Referring now to FIG. 12, the location of the echoes also change as one moves through the phase table, because every X or Y gradient pulse will also add some phase along Z, which must then be refocused with the permanent gradient.

As the resolution of the image is increased, the echoes will begin to approach the edge of the acquisition window. The graphical representation 800 shows how the spin echo moves in time relative to the amount of phase encodes. The black line 810 shows the center of the acquisition window. If the time and the phase are not accounted for correctly then the spin echo could be outside of the acquisition window and missed, effectively truncating k-space and image quality.

When no pulsed gradient is applied, the spin echo will occur after the refocusing pulse, with the time after being determined by the duration of the excitation pulse and the delay between the excitation pulse and refocusing pulse. If a phase encode is applied during this period, the phase it imparts on the system should not be refocused. The X and Y components of a phase encode done with a surface gradient coil will not be refocused during a spin echo sequence, ensuring that the signal is spatially encoded. However, the phase encode will also impart Z phase onto the signal. This Z phase is along the same axis as the permanent gradient, which means that its presence will change when the echo forms.

If the phase along the Z axis needs to be refocused before the echo forms, then adding Z phase with a pulsed gradient will change when the echo forms. For example, if a gradient is applied after excitation, the phase that will be accumulated between the excitation pulse and the refocusing pulse will be equal to the sum of the phase accumulated due to the permanent gradient and the phase accumulated due to the pulsed gradient. If the pulsed gradient is the same sign as the permanent gradient, then the two will add. Thus, after the refocusing pulse, more time will be needed for the echo to occur because both the phase of the permanent gradient and the phase of the pulsed gradient will be refocused by the permanent gradient. This will make the echo appear later then it would otherwise. The stronger the pulsed gradient, the later the echo will appear. Changing the sign of the pulsed gradient can also have the opposite effect, making the echo appear sooner than expected. This can have catastrophic effects on the imaging sequence.

In an imaging sequence, the acquisition period is defined for a fixed amount of time. The length of the acquisition period cannot be arbitrarily changed without altering the pulse sequence in many other ways. For example, most single-sided scanners work by collecting a train of spin echoes, with the time between the refocusing pulses kept as small as possible. This means that the acquisition period between the refocusing pulses are also kept as small as possible. So, if the location of the echo changes as one progresses through the imaging sequence, it is possible that the echo will occur before or after the acquisition period begins. This means that the signal for that phase encode will be lost.

As a result of the Z phase that is added to the signal by the pulsed X and Y gradients, there is effectively a maximum resolution that can be achieved without having to increase the echo spacing of the pulse sequence. The echoes produced at the edges of the k-space, when the pulsed gradients are strong, can be lost, resulting in a k-space where the signal amplitude drops earlier than otherwise. K-space is effectively being truncated, which generally leads to the need to collect a wider acquisition, which will require sacrificing signal-to-noise ratio (SNR) to get a longer echo time.

To summarize, using a surface gradient coil with a single-sided MRI scanner, something that is necessary in order for the scanner to be single-sided, results in a changing field of view along the Z axis, a drifting echo, and ultimately in the truncation of k-space. This effectively limits the image quality of a single-sided MRI scanner.

In accordance with various aspects of the present disclosure, it is possible to compensate for added phase by applying a phase encode during a frequency sweep, or chirped, excitation pulse. A frequency sweep pulse can affect spins at different frequencies at different times during a pulse. This means that it is also possible to impart different amounts of phase to different frequencies by applying a phase encode during an excitation pulse. The spins excited at the beginning of the pulse can accumulate more phase than the spins excited at the end of the pulse, which can accumulate little phase.

In accordance with various aspects, if the spins further from the permanent magnet are excited first, and if a phase encode is applied during the frequency sweep excitation pulse, then those farther away spins can accumulate more phase than the spins closer to the permanent magnet, which can be excited last. This can invert the usual way spins accumulate phase from a surface gradient coil, allowing one to counter the normal variation in gradient strength along the Z axis. By precisely tuning the amount of phase accumulated during the frequency sweep excitation and during a subsequent phase encode, it is possible to apply an even amount of phase to the X-Y plane along the Z axis of the permanent magnet.

Figure 13:
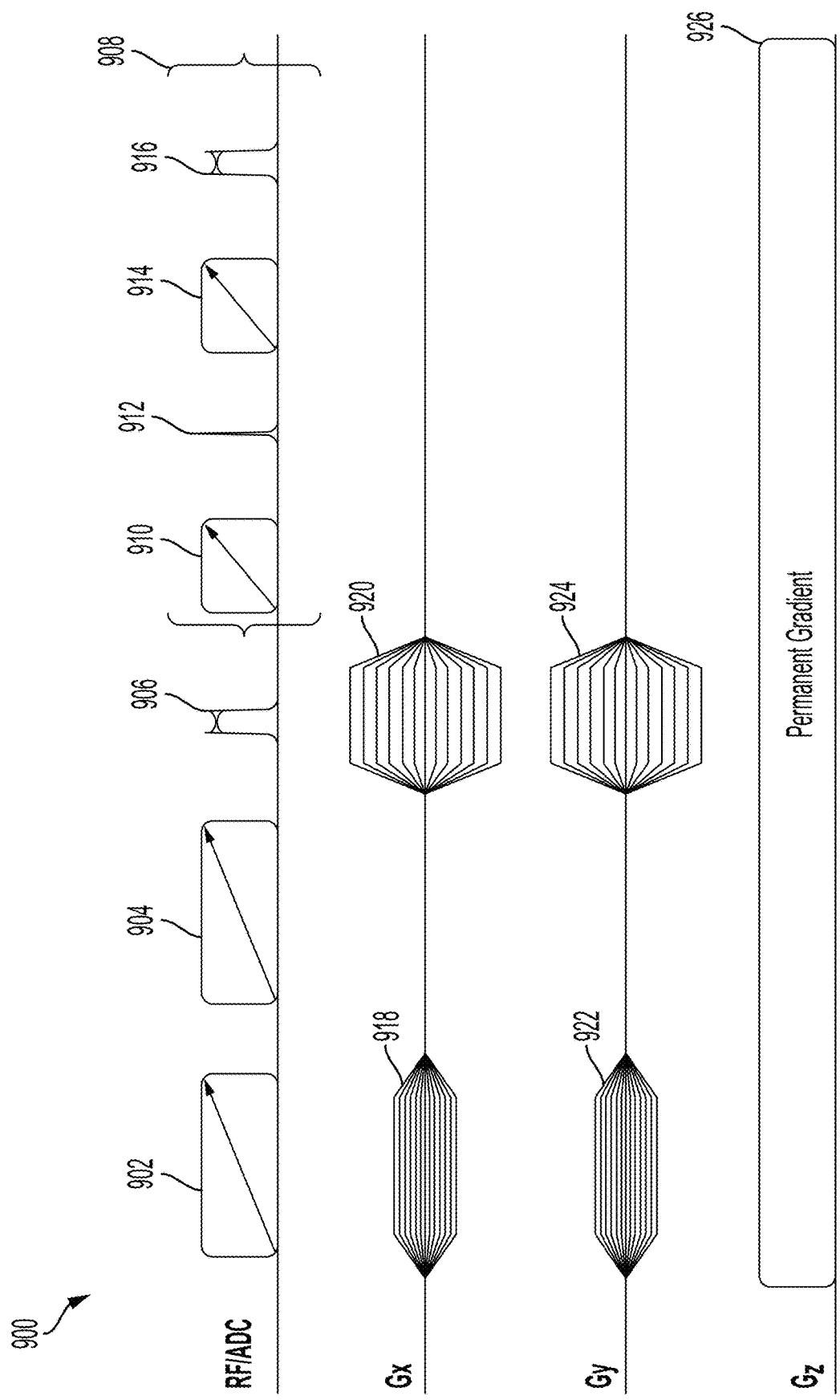
FIG. 13 is a diagram of a pulse sequence that compensates for the varying field of view in slices along the Z axis, according to various aspects of the present disclosure.

FIG. 13 shows a pulse sequence 900 that is configured to compensate for the varying field of view in slices along the Z axis produced by surface gradient coils (see, e.g. gradient coils 152, 154 in FIG. 6) This compensation is achieved with phase encoding applied during a frequency sweep excitation pulse. In various instances, the frequency sweep pulses described herein are chirp or chirped pulses having a linear frequency sweep. A chirped excitation pulse can define a linear frequency sweep from low to high. Other monotonic low-to-high frequency increases are also contemplated. The low frequencies excite tissue farther from the permanent magnet assembly (see, e.g. the permanent magnet assembly 130 in FIG. 2) and the high frequencies excite tissue closer to the permanent magnet assembly, so by the end of the pulse, slices further from the magnet will have been phase encoded for more time, compensating for the gradient being weaker. The first pulse 902 in the pulse sequence is a frequency sweep excitation pulse 902, with the chirp frequency swept direction set from low to high. The gradients in the X and Y directions begin to dephase 918 and 922, respectively, and are refocused by the second pulse 904 in the pulse sequence. The gradient in Z is constant during the entire pulse sequence. The second pulse 904 is a refocusing pulse that refocuses the X and Y gradients. After the second pulse 904, a spectral echo 906 occurs where the X and Y gradients dephase 920 and 924, respectively. After the spectral echo 906, the signal is then read out with a chirped echo train 908. The chirped echo train 908 comprises a third pulse 910, a spin echo 912, a fourth pulse 914, and a spectral echo 916. In one aspect, the third pulse 910 may be a second refocusing pulse and the fourth pulse 914 may be a second excitation pulse.

In this implementation, the changing field of view is overcompensated during the excitation pulse and then balanced with the phase encode. The amount of phase accumulated during the frequency sweep needs to be precisely tuned to apply an even amount of phase to the X-Y plane of the slices being imaged. Stated another way, the amount of phase in each slice needs precisely tuned to account for the changing field of view. Stated yet another way, the scale of the object in each slice needs to be adjusted so that all the slices have the object scaled the same. For example, the tuning can be performed by adjusting the power of the gradient pulse applied during the frequency sweep pulse while collecting a 2D image along the X-Z or Y-Z axes. The gradient power can be increased until the size of the object does not change along the Z axis. Then, the slices can be combined into a high quality slab image without any blurring occurring from the combination.

Figure 14:
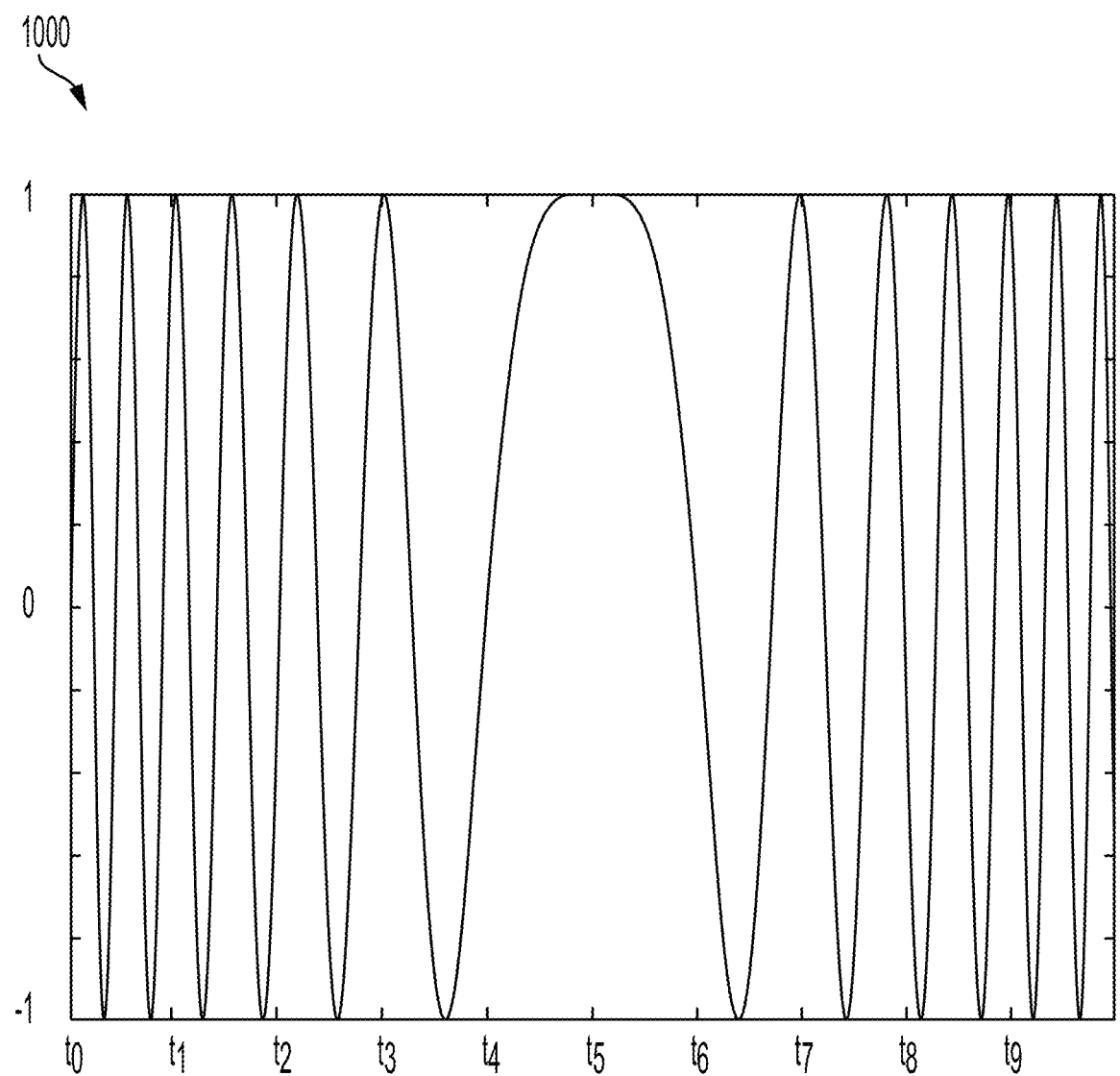
FIG. 14 is a representative graph of a sweeping frequency pulse, according to various aspects of the present disclosure.

FIG. 14 shows a representative graph 1000 of a sweeping frequency pulse or chirp pulse, where the swept direction is set from low to high. A chirped excitation pulse, with the swept direction set from low to high, is an example of a frequency sweep excitation pulse. The frequency of a chirp pulse with the swept direction set from low to high begins at a low frequency and the frequency increases through time for the duration of the pulse. The pulse can begin at the lowest frequency desired and ends once the maximum desired frequency is reached. The pulse frequency in the graph 1000 can be a negative-to-positive frequency offset to the baseband frequency. In other words, the frequency sweeps from negative to positive plus the baseband frequency. For example, for a frequency sweep of +/−100 KHz, the sweep is from the baseband frequency less 100 KHz to the baseband frequency plus 100 KHz.

The frequency of a chirp pulse can vary from a minimum (lowest) desired frequency to a maximum (highest) desired frequency. The sweep rate of the pulse is the difference between the highest frequency and lowest frequency in the pulse divided by the time required to go between the highest frequency and the lowest frequency. In one aspect, the frequency range that is covered by the sweeping frequency pulses used in the sweeping frequency pulse sequence 900 may be from −20 KHz to 20 KHz, i.e. a 40 KHz range, with a center frequency that varies slab to slab. For example, a slab could be centered at 2.62 MHz, 2.75 MHz, 2.65 MHz, 2.72 MHz, 2.79 MHz, 2.69 MHz, and so on. For a slab centered at 2.62 MHz, the chirp pulse would sweep from 2.60 MHz to 2.64 MHz, i.e. a 40 KHz range. In other aspects of the present disclosure, bandwidths as low as 10 KHz to as high as 200 KHz may be used in the frequency sweep pulse. Moreover, the sweep range can be less than 40 KHz in various instances.

Referring again to FIG. 9, $f_0$ can corresponds to the lowest frequency of the chirp pulse and $f_n$ can corresponds to the highest frequency of the chirp pulse. The chirp pulse excites tissue farther away from the permanent magnet assembly first, such as tissue at the location of $slice_0$, and excites the tissue close to the permanent magnet assembly later, such as the tissue at the location of $slice_n$. Stated another way, adjacent slices comprise a proximal slice and a distal slice, where the proximal slice is positioned closer to the magnetic imaging apparatus than the distal slice, and a target in the distal slice is excited before a target in the proximal slice. The frequency range of the chirp pulse may correspond to the slices of the slab being imaged.

Referring again to FIG. 13, the first pulse 902 is a chirped excitation pulse with the swept direction set from low to high. This pulse excites tissue in slices farther from the permanent magnet assembly before exciting tissue in slices closer to the permanent magnet assembly. By phase encoding during the chirped excitation there is a different amount of phase accumulated at different frequencies. Specifically, the slices farther away from the permanent magnet assembly accumulate more phase than slices closer to the permanent magnet assembly. Stated another way, the target in the slices that are more distal from the permanent magnet assembly accumulate more phase than the target in the slices that are more proximal to the permanent magnet assembly. Phase encoding during the frequency sweep excitation pulse along with the tuning of the phase accumulated in each slice can account for the phases in each slice and keep the echo from drifting outside of the acquisition window 810 (FIG. 12). After accounting for the changing field of view in slices along the Z axis, the slices can be combined into a slab to produce a high quality axial image, where the scale of the object in each slice is the same size.

Figure 15:
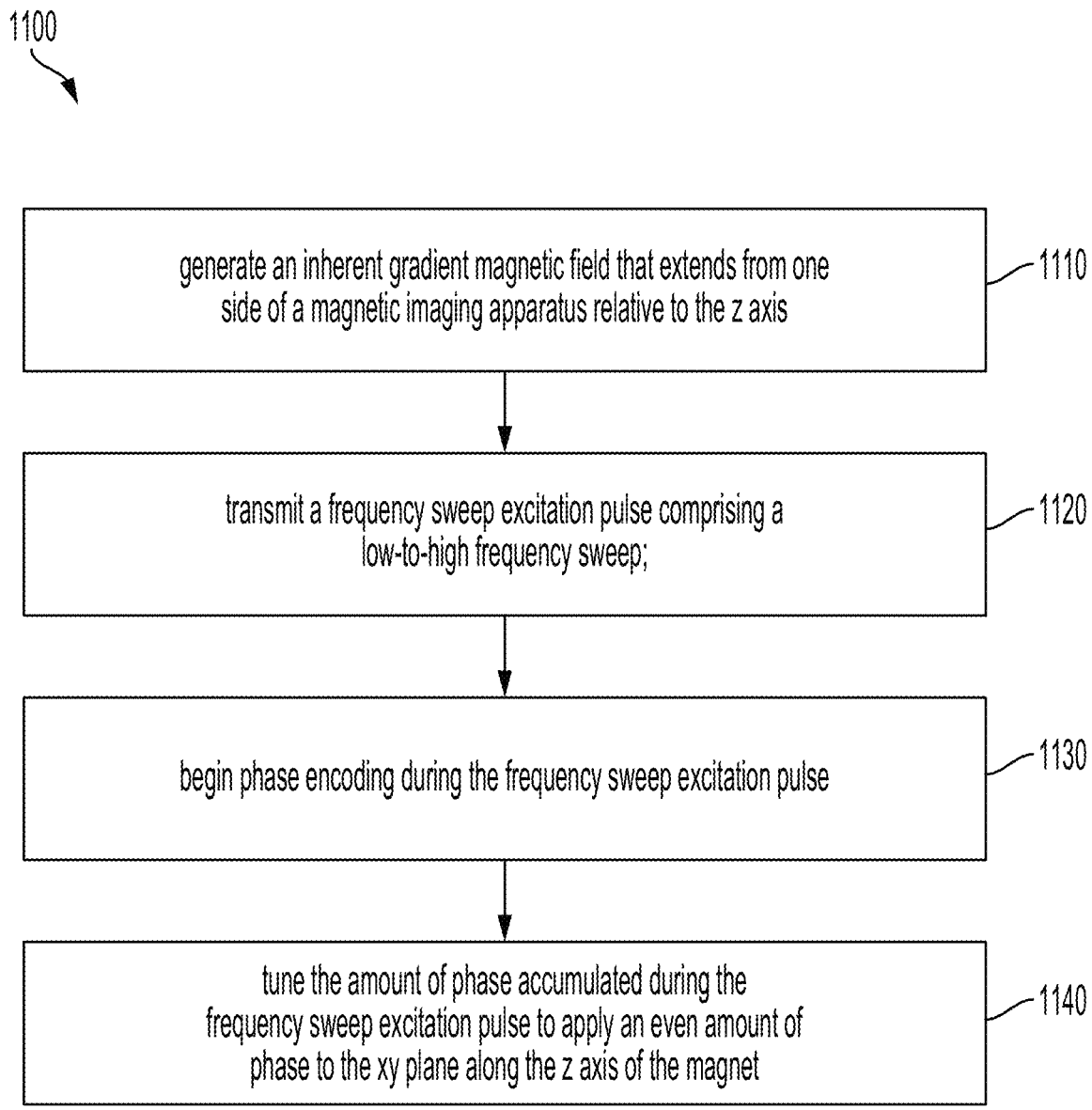
FIG. 15 is a flow diagram of steps in a pulse sequence that account for the changing field of view in the slices along the Z axis, according to various aspects of the present disclosure.

FIG. 15 is a flow diagram 1100 for the steps in a pulse sequence to account for the changing field of view in the slices along the Z axis. At 1110, the process begins upon the generation of an inherent gradient magnetic field that extends from one side of a magnetic imaging apparatus relative to the Z axis (FIG. 1) into the field of view. Then, at 1120, a frequency sweep excitation pulse is transmitted, which comprises a low-to-high frequency sweep. This pulse excites tissue at locations/slices farther from the one-sided MRI scanner first and tissue at locations closer to the MRI scanner last. At 1130, phase encoding begins during the frequency sweep excitation pulse of 1120. The phase encoding may be done during the frequency sweep excitation pulse to accumulate a different amount of phase in different frequencies of the frequency sweep. The slices relate to the frequency and the frequencies farther from the magnetic imaging apparatus accumulate more phase than the slices closer to imaging apparatus. Finally, at 1140, the amount of phase accumulated during the frequency sweep excitation pulse is tuned to apply an even amount of phase to the X-Y plane along the Z axis of the magnet. Stated another way, the amount of phase accumulated in the slices during the frequency sweep is tuned so that the changing field of view for each slice can be adjusted for. For example, the tuning can be performed by adjusting the power of the gradient pulse applied during the chirp pulse while collecting a 2D image along the X-Y or Y-Z planes. The gradient power can be increased until the size of the object does not change along the Z axis. After the tuning step, the signal is read out with a chirped echo train. For example, the goal of accounting for the changing field of view is to have the object in each slice have the same scale. Without accounting for the changes in field of view the object in adjacent slices would appear larger or smaller due to how the field of view changed due to the gradient. Combining slices with different field of views results in a blurry axial image or slab. Accounting for the field of view change along the Z axis allows the slices to be combined into a high quality axial image or slab.

By encoding images in this way, several problems with single-sided MRI systems can be resolved, which can allow single-sided MRI systems to be applied more widely. Encoding in this way can prevent the spin echoes from drifting, which prevents them from drifting away from the acquisition window. This can further prevent k-space from being truncated and, thus, allow the single-sided MRI system to collect higher resolution images. The field of view can also stop changing along the Z axis, which makes combining image slices along the Z axis more efficient, resulting in higher SNR and shorter scan times.

Figure 16:
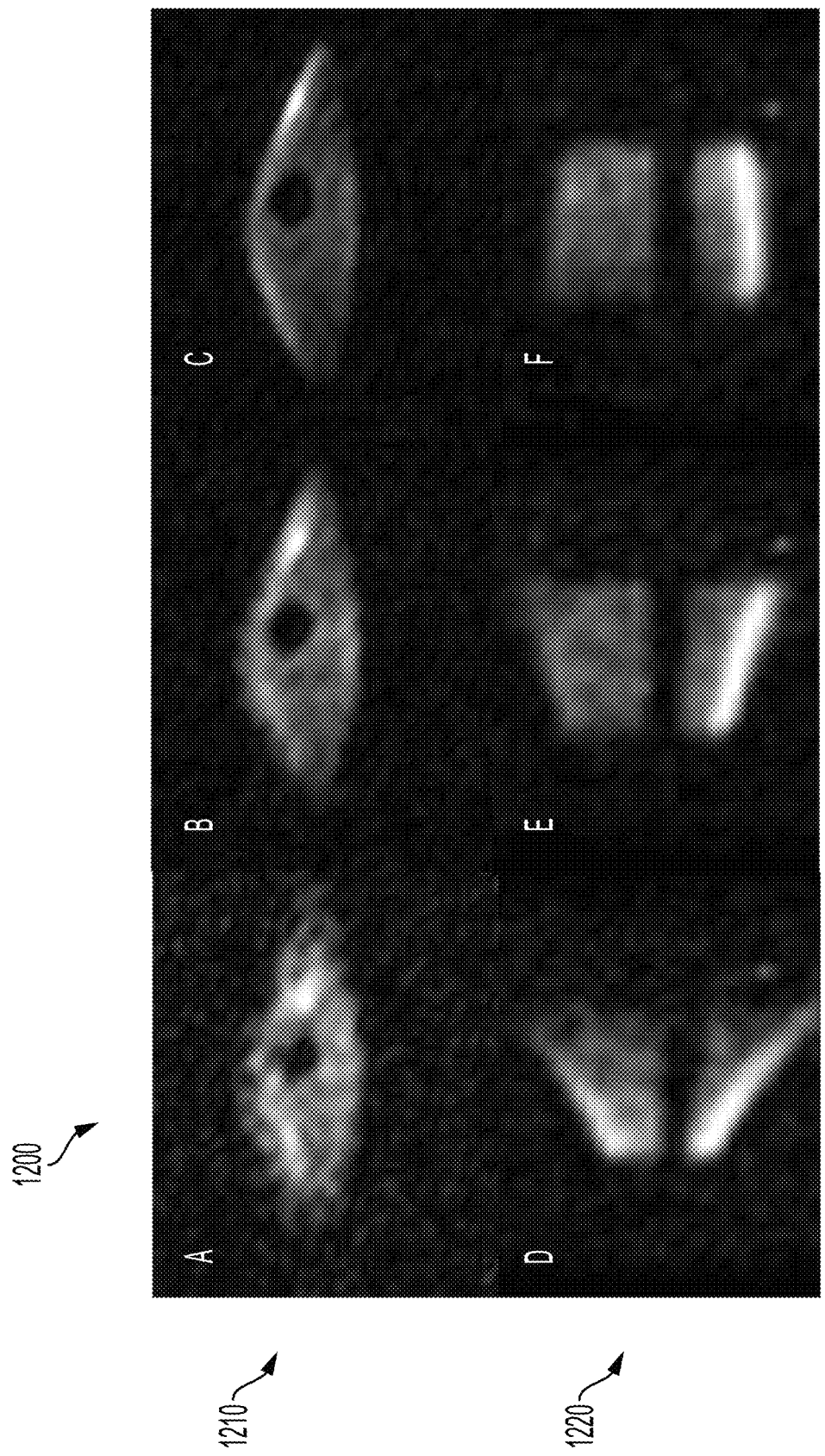
FIG. 16 is a collection of MRI images slices, according to various aspects of the present disclosure.

FIG. 16 shows a collection 1200 of images slices. The images A, B, and C in the top row 1210 show an axial slice from a 3D image collected with X and Y gradients that vary along the Z axis, as well. When the gradients vary significantly, as shown in images A and B in the top row 1210, the axial slice appears blurry. When the variation in gradient is reduced, as shown in image C in the top row 1210, the image appears sharper. Imaging with a changing field of view, limits the maximum slice thickness one can use without drastically reducing image quality because combining slices with different field of views results in a blurry axial image. The bottom row 1220 shows three coronal slices taken from the same 3D images as the top row 1210. The phantom clearly changes in size along one axis for images D and E. The changing in size is due to the varying field of view. Image F shows the object when the varying field of view is accounted for through the process described in FIG. 15.

Figure 17:
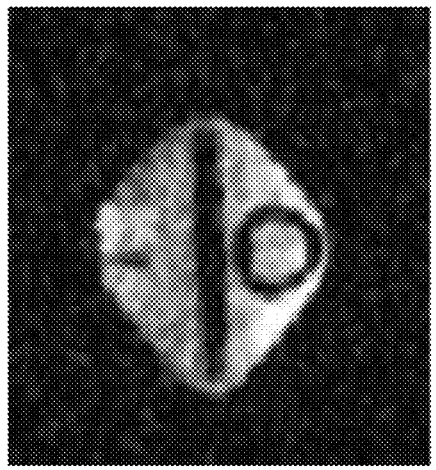
FIG. 17 is a collection of MRI image slices, according to various aspects of the present disclosure.
Figure 17:
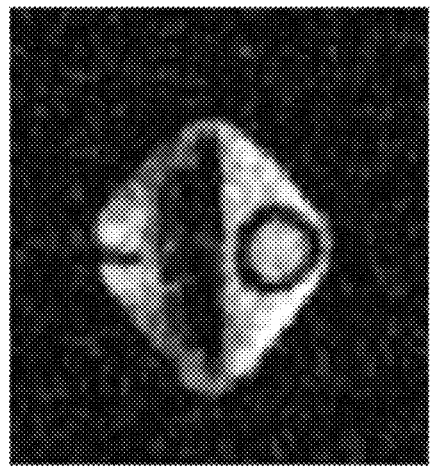
Figure 17:
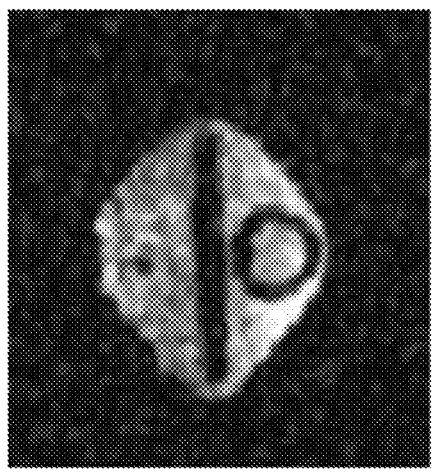
Figure 17:
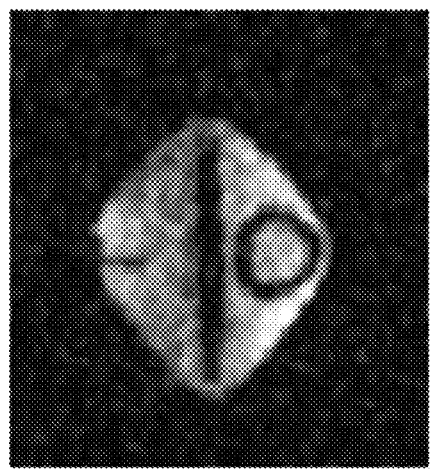

Similarly, FIG. 17 shows a collection 1300 of image slices that had the field of view accounted for by the process described in FIG. 15. Imaging with the process of flow diagram 1100 results in a consistent field of view across different slices. This allows one to combine slices without blurring the image. Imaging with the process of flow diagram 1100 also aligns echoes in time, preventing them from drifting outside the acquisition window which increases resolution.

The foregoing processes and technique can also be utilized with other single-sided scanners and/or inhomogeneous magnetic fields, to allow for faster data and/or image acquisition.

EXAMPLES

Various aspects of the subject matter described herein are set out in the following numbered examples.

Example 1—A method of imaging a slab having at least two slices with a single-sided magnetic imaging apparatus, wherein an inherent gradient magnetic field extends from the magnetic imaging apparatus into a field of view, the method comprising: transmitting a frequency sweep excitation pulse comprising a low-to-high frequency sweep; phase encoding during the frequency sweep excitation pulse; and tuning the amount of phase accumulated during the frequency sweep excitation pulse from adjacent slices in the slab.

Example 2—The method of Example 1, wherein the adjacent slices comprise a proximal slice and a distal slice, wherein the proximal slice is positioned closer to the magnetic imaging apparatus than the distal slice, and wherein a target in the distal slice is excited before a target in the proximal slice.

Example 3—The method of Example 2, wherein the method is configured to compensate for the inherent gradient magnetic field such that the target in the distal slice accumulates the same phase as the target in the proximal slice.

Example 4—The method of any of Examples 1, 2, and 3, wherein a different amount of phase is applied to different frequencies in the frequency sweep.

Example 5—The method of any of Examples 1, 2, 3, and 4, wherein the phase encoding during the frequency sweep excitation pulse prevents an echo from drifting outside of an acquisition window.

Example 6—The method of any of Examples 1, 2, 3, 4, and 5, wherein high resolution images are collected with the single-sided magnetic imaging apparatus without k-space truncation.

Example 7—The method of any of Examples 1, 2, 3, 4, 5, and 6, wherein the magnetic field strength in the field of view is less than 1 Tesla.

Example 8—The method of any of Examples 1, 2, 3, 4, 5, 6, and 7, wherein the inhomogeneity of the magnetic field is between 200 ppm and 200,000 ppm.

Example 9—A magnetic imaging apparatus, comprising: a permanent magnet; a gradient coil set; an electromagnet; a radio frequency coil, wherein an inherent gradient magnetic field extends from the magnetic imaging apparatus relative to a first axis into the field of view, wherein the first axis is perpendicular to the permanent magnet; and a control circuit configured for imaging a slab having at least two slices, wherein the imaging comprises: transmitting a frequency sweep excitation pulse comprising a low-to-high frequency sweep; phase encoding during the frequency sweep excitation pulse; and tuning the amount of phase accumulated during the frequency sweep excitation pulse from adjacent slices in the slab.

Example 10—The magnetic imaging apparatus of Example 9, wherein the adjacent slices comprise a proximal slice and a distal slice, wherein the proximal slice is positioned closer to the magnetic imaging apparatus than the distal slice, and wherein a target in the distal slice is excited before a target in the proximal slice.

Example 11—The magnetic imaging apparatus of Example 10, wherein a different amount of phase is applied to different frequencies.

Example 12—The magnetic imaging apparatus of Example 11, wherein the target in the distal slice accumulates the same phase as the target in the proximal slice.

Example 13—The magnetic imaging apparatus of any of Examples 9, 10, 11, and 12, wherein the phase encoding during the frequency sweep excitation pulse prevents an echo from drifting outside of an acquisition window.

Example 14—The magnetic imaging apparatus of any of Examples 9, 10, 11, 12, and 13, wherein high resolution images are collected with the single-sided magnetic imaging apparatus without k-space truncation.

Example 15—The magnetic imaging apparatus of any of Examples 9, 10, 11, 12, 13, and 14 wherein magnetic field strength in the field of view is less than 1 Tesla.

Example 16—The magnetic imaging apparatus of any of Examples 9, 10, 11, 12, 13, 14, and 15, wherein the inhomogeneity of the magnetic field is between 200 ppm and 200,000 ppm.

Example 17—The magnetic imaging apparatus of any of Examples 9, 10, 11, 12, 13, 14, 15, and 16, wherein the radio frequency coil comprises a radio frequency transmission coil and a radio frequency reception coil.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion, or housing, of a surgical instrument. The term "proximal" refers to the portion closest to the clinician and/or to the robotic arm and the term "distal" refers to the portion located away from the clinician and/or from the robotic arm. It will be further appreciated that, for convenience and clarity, spatial terms such as "vertical", "horizontal", "up", and "down" may be used herein with respect to the drawings. However, robotic surgical tools are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A method of imaging a slab having at least two slices with a single-sided magnetic imaging apparatus, wherein an inherent gradient magnetic field extends from the magnetic imaging apparatus into a field of view, the method comprising:
   transmitting a frequency sweep excitation pulse via the magnetic imaging apparatus, wherein the frequency sweep excitation pulse comprises a low-to-high frequency sweep;
   phase encoding during the frequency sweep excitation pulse;
   tuning the amount of phase accumulated during the frequency sweep excitation pulse from adjacent slices in the slab, wherein the tuning is performed by the magnetic imaging apparatus;
   wherein the adjacent slices comprise a proximal slice and a distal slice, wherein the proximal slice is positioned closer to the magnetic imaging apparatus than the distal slice, and wherein a target in the distal slice is excited before a target in the proximal slice; and
   collecting images of the adjacent slices with the magnetic imaging apparatus to generate the slab;
   wherein the method is configured to compensate for the inherent gradient magnetic field such that the target in the distal slice accumulates the same phase as the target in the proximal slice.

2. A magnetic imaging apparatus, comprising:
   a permanent magnet;
   a gradient coil set;
   an electromagnet;
   a radio frequency coil, wherein an inherent gradient magnetic field extends from the magnetic imaging apparatus relative to a first axis into the field of view, wherein the first axis is perpendicular to the permanent magnet; and
   a control circuit configured for imaging a slab having at least two slices, wherein the imaging comprises:
      transmitting a frequency sweep excitation pulse comprising a low-to-high frequency sweep;
      phase encoding during the frequency sweep excitation pulse;
      tuning the amount of phase accumulated during the frequency sweep excitation pulse from adjacent slices in the slab; and
      collecting images of the adjacent slices to generate the slab;
      wherein (i) a different amount of phase is applied to different frequencies or (ii) the phase encoding during the frequency sweep excitation pulse prevents an echo from drifting outside of an acquisition window.

3. A method of imaging a slab having at least two slices with a single-sided magnetic imaging apparatus, wherein an inherent gradient magnetic field extends from the magnetic imaging apparatus into a field of view, the method comprising:
   transmitting a frequency sweep excitation pulse via the magnetic imaging apparatus, wherein the frequency sweep excitation pulse comprises a low-to-high frequency sweep;
   phase encoding during the frequency sweep excitation pulse
   tuning the amount of phase accumulated during the frequency sweep excitation pulse from adjacent slices in the slab, wherein the tuning is performed by the magnetic imaging apparatus; and
   collecting images of the adjacent slices to generate the slab;
   wherein a different amount of phase is applied to different frequencies in the frequency sweep.

4. A method of imaging a slab having at least two slices with a single-sided magnetic imaging apparatus, wherein an inherent gradient magnetic field extends from the magnetic imaging apparatus into a field of view, the method comprising:
   transmitting a frequency sweep excitation pulse via the magnetic imaging apparatus, wherein the frequency sweep excitation pulse comprises a low-to-high frequency sweep;
   phase encoding during the frequency sweep excitation pulse, wherein the phase encoding during the frequency sweep excitation pulse prevents an echo from drifting outside of an acquisition window
   tuning the amount of phase accumulated during the frequency sweep excitation pulse from adjacent slices in the slab, wherein the tuning is performed by the magnetic imaging apparatus; and
   collecting images of the adjacent slices to generate the slab.

5. The method of claim 1, wherein a different amount of phase is applied to different frequencies in the frequency sweep.

6. The method of claim 1, wherein the phase encoding during the frequency sweep excitation pulse prevents an echo from drifting outside of an acquisition window.

7. The method of claim 1, wherein high resolution images are collected with the single-sided magnetic imaging apparatus without k-space truncation.

8. The method of claim 1, wherein the magnetic field strength in the field of view is less than 1 Tesla.

9. The method of claim 1, wherein the inhomogeneity of the magnetic field is between 200 ppm and 200,000 ppm.

10. The magnetic imaging apparatus of claim 2, wherein the adjacent slices comprise a proximal slice and a distal slice, wherein the proximal slice is positioned closer to the magnetic imaging apparatus than the distal slice, and wherein a target in the distal slice is excited before a target in the proximal slice.

11. The magnetic imaging apparatus of claim 2, wherein high resolution images are collected with the single-sided magnetic imaging apparatus without k-space truncation.

12. The magnetic imaging apparatus of claim 2, wherein magnetic field strength in the field of view is less than 1 Tesla.

13. The magnetic imaging apparatus of claim 2, wherein the inhomogeneity of the magnetic field is between 200 ppm and 200,000 ppm.

14. The magnetic imaging apparatus of claim 2, wherein the radio frequency coil comprises a radio frequency transmission coil and a radio frequency reception coil.

15. The magnetic imaging apparatus of Claim 10, wherein the target in the distal slice accumulates the same phase as the target in the proximal slice.

* * * * *